United States Patent
You et al.

(10) Patent No.: US 11,572,540 B2
(45) Date of Patent: Feb. 7, 2023

(54) METHOD FOR INDUCING OLIGODENDROCYTE PRECURSOR CELLS FROM OCT4-INDUCED HUMAN SOMATIC CELLS THROUGH DIRECT REPROGRAMMING

(71) Applicant: Stemlab Inc., Seoul (KR)

(72) Inventors: Seung Kwon You, Yongin-si (KR); Won-Jin Yun, Yongin-si (KR); Min Ji Park, Usan (KR); Ji-Yong Park, Daegu (KR)

(73) Assignee: Stemlab Inc., Seoul (KR)

( * ) Notice: Subject to any disclaimer, the term of this patent is extended or adjusted under 35 U.S.C. 154(b) by 358 days.

(21) Appl. No.: 16/992,136

(22) Filed: Aug. 13, 2020

(65) Prior Publication Data
US 2021/0017491 A1 Jan. 21, 2021

Related U.S. Application Data

(62) Division of application No. 16/429,062, filed on Jun. 3, 2019, now Pat. No. 10,767,163, which is a division of application No. 15/575,369, filed as application No. PCT/KR2016/004603 on May 2, 2016, now abandoned.

(30) Foreign Application Priority Data

May 19, 2015 (KR) .................. 10-2015-0069696
Apr. 8, 2016 (KR) .................. 10-2016-0043593

(51) Int. Cl.
*C12N 5/079* (2010.01)

(52) U.S. Cl.
CPC ...... *C12N 5/0622* (2013.01); *C12N 2501/065* (2013.01); *C12N 2501/115* (2013.01); *C12N 2501/135* (2013.01); *C12N 2501/15* (2013.01); *C12N 2501/235* (2013.01); *C12N 2501/2306* (2013.01); *C12N 2501/41* (2013.01); *C12N 2501/603* (2013.01); *C12N 2501/727* (2013.01); *C12N 2501/999* (2013.01); *C12N 2506/00* (2013.01); *C12N 2506/1307* (2013.01)

(58) Field of Classification Search
None
See application file for complete search history.

(56) References Cited

U.S. PATENT DOCUMENTS

| | | |
|---|---|---|
| 2012/0282228 A1 | 11/2012 | Bhasin |
| 2015/0030570 A1 | 1/2015 | Pan et al. |
| 2018/0010094 A1 | 1/2018 | Hong et al. |
| 2018/0155685 A1 | 6/2018 | You et al. |
| 2019/0284528 A1 | 9/2019 | You et al. |

FOREIGN PATENT DOCUMENTS

| | | |
|---|---|---|
| KR | 10-2013-0085767 | 7/2013 |
| KR | 10-1357402 | 2/2014 |
| WO | WO 2016/167528 | 10/2016 |

OTHER PUBLICATIONS

Steelman et al, Neurobiology of Disease, Apr. 6, 2016, 91:336-346. (Year: 2016).*
Joubert et al, Journal of Neuroscience Research, 2010, 88:2546-2557. (Year: 2010).*
International Search Report dated Jul. 29, 2016 From the Korean Intellectual Property Office Re. Application No. PCT/KR2016/004603. (2 Pages).
Notice of Allowance dated May 20, 2020 from the US Patent and Trademark Office Re. U.S. Appl. No. 16/429,062. (11 pages).
Official Action dated Mar. 4, 2019 From the US Patent and Trademark Office Re. U.S. Appl. No. 15/575,369. (13 Pages).
Official Action dated Nov. 5, 2018 From the US Patent and Trademark Office Re. U.S. Appl. No. 15/575,369. (11 pages).
Restriction Official Action dated Aug. 10, 2018 From the US Patent and Trademark Office Re. U.S. Appl. No. 15/575,369. (8 pages).
Supplementary European Search Report and the European Search Opinion dated Oct. 17, 2018 From the European Patent Office Re. Application No. 16796673.8.
Translation of Written Opinion dated Jul. 29, 2016 From the Korean Intellectual Property Office Re. Application No. PCT/KR2016/004603. (2 Pages).
Goldman et al. "How to Make an Oligodendrocyte", Development, XP055512509, 142(23): 3983-3995, Dec. 2015.
Hu et al. "Direct Conversion of Normal and Alzheimer's Disease Human Fibroblasts Into Neuronal Cells by Small Molecules", Cell Stem Cell, XP055377446, 17(2): 204-212, Aug. 6, 2015.
Johe et al. "Single Factors Direct the Differentiation of Stem Cells From the Fetal and Adult Central Nervous System", Genes & Development, 10(24): 3129-3140, Dec. 15, 1996.
Kerr et al. "Leukemia Inhibitory Factor Promotes Oligodendrocyte Survival After Spinal Cord Injury", GLIA, 51(1): 73-79, Published Online Mar. 18, 2005.
Kim et al. "Direct Reprogramming of Mouse Fibroblasts to Neural Progenitors", Proc. Natl. Acad. Sci. USA, PNAS, 108(19): 7838-7843, May 10, 2011.
Kim et al. "Oct4-Induced Oligodendrocyte Progenitor Cells Enhance Functional Recovery in Spinal Cord Injury Model", The EMBO Journal, XP055512518, 34(23): 2971-2983, Published Online Oct. 23, 2015.
Mitchell et al. "Molecular Evidence for OCT4-Induced Plasticity in Adult Human Fibroblasts Required for Direct Cell Fate Conversion to lineage Specific Progenitors", Stem Cells, 32(8): 2178-2187, Published Online Apr. 16, 2014.

(Continued)

*Primary Examiner* — Allison M Fox

(57) ABSTRACT

Provided is a method of inducing oligodendrocyte precursor cells (OPCs) through direct reprogramming from human somatic cells into which a nucleic acid molecule encoding an Oct4 protein or Oct4 protein-treated human somatic cells. The method of inducing OPCs by treating Oct4-overexpressing human somatic cells with a low molecular weight substance may establish OPCs with high efficiency in a short period of time through direct reprogramming without via neural stem cells, and thus the OPCs are useful as a cell therapeutic agent for an intractable demyelinating disease.

12 Claims, 19 Drawing Sheets

(56) References Cited

OTHER PUBLICATIONS

Moon et al. "Reprogramming Fibroblasts into Induced Pluripotent Stem Cells with Bmi1", Cell Research, 21: 1305-1315, 2011.

Najm et al. "Transcription Factor-Mediated Reprogramming of Fibroblasts to Expandable, Myelinogenic Oligodendrocyte Progenitor Cells", Nature Biotechnology, XP055106732, 31(5): 426-433, Published Online Apr. 14, 2013. Abstract, p. 427, Fig.1.

Nishiyama et al. "Polvdendrocytes (NG2 Cells): Multifunctional Cells with Lineage Plasticity", Nature Review Neuroscience, 10: 9-22, Jan. 2009.

Pedraza et al. "Induction of Oligodendrocyte Differentiation and In Vitro Myelination by Inhibition of Rho-Associated Kinase", ASN Neuro, 6(4): e1759091414538-1-e1759091414538-17, May-Jun. 2014. Abstract.

Sigma-Aldrich "Dulbecco's Modified Eagle's Medium/Ham's Nutrient Mixture F-12 (DME/F12) Formulation", Sigma Aldrich Cell Culture, 4., Oct. 29, 2018.

Yang et al. "Generation of Oligodendroglial Cells by Direct Lineage Conversion", Nature Biotechnology, XP055223240, 31(5): 434-439, Published Online Apr. 14, 2013.

Zheng et al. "A Combination of Small Molecules Directly Reprograms Mouse Fibroblasts Into Neural Stem Cells", Biochemical and Biophysical Research CommunicationsXP029567647, 476(1): 42-48, Available Online May 17, 2016.

Zhou et al. "Generation of Induced Pluripotent Stem Cells Using Recombinant Proteins", Cell Stem Cell, 4(5): 381-384, May 8, 2009.

* cited by examiner

EAE mouse model
PBS injection

EAE mouse model
iOPC transplantation

Normal mouse

METHOD FOR INDUCING OLIGODENDROCYTE PRECURSOR CELLS FROM OCT4-INDUCED HUMAN SOMATIC CELLS THROUGH DIRECT REPROGRAMMING

RELATED APPLICATIONS

This application is a division of U.S. patent application Ser. No. 16/429,062 filed on Jun. 3, 2019, which is a division of U.S. patent application Ser. No. 15/575,369 filed on Nov. 19, 2017, which is a National Phase of PCT Patent Application No. PCT/KR2016/004603 having International filing date of May 2, 2016, which claims the benefit of priority of Korean Patent Applications Nos. 10-2015-0069696 filed on May 19, 2015, and 10-2016-0043593 filed on Apr. 8, 2016. The contents of the above applications are all incorporated by reference as if fully set forth herein in their entirety.

FIELD AND BACKGROUND OF THE INVENTION

The present invention relates to a method of inducing oligodendrocyte precursor cells (OPCs) through direct reprogramming from human somatic cells into which a nucleic acid molecule encoding an Oct4 protein has been introduced or Oct4 protein-treated human somatic cells.

Due to the progression of an aging society, personalized cell therapeutic agents for healthier aging and a healthy life without disease are medications essential for improving the quality of life. Multiple sclerosis known as a disease of the central nervous system is a demyelinating disease whose cause is unknown, and in severe cases, is accompanied by sensory and motor impairment. However, there is no fundamental therapy, except treatment with medications for reducing symptoms. Accordingly, transplantation of OPCs (OPC) that can differentiate into oligodendrocytes enabling the generation of myelin sheaths has attracted attention as a main therapeutic method, and research to obtain cells which will be used for the transplantation is progressing using embryonic stem cells and adult stem cells.

Embryonic stem cells are pluripotent cells which are able to differentiate into all types of human cells having the ability to divide indefinitely, unlike somatic cells. Adult stem cells are multipotent cells which are able to be extracted from a patient, and as a representative example, neural stem cells (NSCs) are well known. NSCs, which are adult stem cells, can overcome immune rejection in the treatment of neurological diseases, and therefore has attracted attention as a cell therapeutic agent. However, NSCs are not effective because they have a considerably low ability to differentiate into oligodendrocytes, and are limited in number of cells because they should be obtained from a patient's own cerebral tissue. Embryonic stem cells also have disadvantages to be overcome for clinical use. First, there is an ethical issue because it is necessary to destroy a fertilized embryo to obtain embryonic stem cells, and when cells differentiated from the embryonic stem cells are transplanted into a patient, immune rejection occurs.

Among various methods attempting to overcome such problems, a method of dedifferentiation from differentiated cells to undifferentiated cells has attracted attention, and dedifferentiation encompasses the generation of pluripotent stem cells such as embryonic stem cells using differentiated cells. After induced pluripotent stem cells (iPS cells) were developed through gene introduction by Prof. Shinya Yamanaka, Japan in 2006, a variety of studies for applying such cells to a therapeutic agent are progressing.

After the report in which stem cells having similar characteristics to embryonic stem cells are established when four genes (dedifferentiation-inducible factors; Oct4, Sox2, c-Myc and Klf4) were introduced into mouse or human somatic cells, and then cultured under embryonic stem cell culture conditions for a long time (Cell 126:663-676, 2006; Science 318:1917-1920, 2007) had been suggested, various methods capable of replacing genes for clinical use have been studied. However, because of still insufficient results of the study on human somatic cells, difficulty in defining a dedifferentiation-inducing mechanism, and a risk of forming teratoma, it is difficult to apply iPS cells to clinical trials. A direct reprogramming method is a method which has been recently suggested as an alternative for such iPS cells, and includes two types of techniques for introducing genes specifically expressed in cells and inducing the cells to desired cells without the pluripotency stage through the regulation of a growth signal by combination of dedifferentiation-inducible factors and low molecular weight substances. Such a method is highly appreciated in that it has only advantages of various stem cells, and eliminates many of the factors which inhibit a clinical use.

In recent years, the possibility of establishment of mouse OPCs has been shown by the Marius Wernig research team using three genes (Olig2, Sox10, Zfp536) and by the Paul J Tesar research team using three genes (Olig2, Sox10, NKX6.2) in the United States, and it has been reported that they made a success of direct reprogramming from mouse somatic cells to OPCs. However, there is no still report in which human somatic cells are used. In addition, the Shengding and Mickie Bhatia research teams in the United States demonstrated the establishment of neural stem cells through direct reprogramming by introducing an Oct4 gene into a human somatic cell, and thus suggested a new paradigm in which the Oct4 gene can regulate the expression of nervous system-related genes in cells.

Therefore, the inventors intensively attempted to induce OPCs from human somatic cells through direct reprogramming, resulting in confirming the possibility of induction of OPCs by introducing Oct4 into human somatic cells and treating several low molecular weight substances involved in forming oligodendrocytes, and thus completed the present invention.

SUMMARY OF THE INVENTION

The present invention is directed to providing a method of inducing OPCs from human somatic cells through direct reprogramming, which includes culturing human somatic cells into which a nucleic acid molecule encoding an Oct4 protein is introduced into a medium containing specific low molecular weight substances.

The present invention is also directed to providing a method of inducing OPCs from human somatic cells through direct reprogramming, which includes culturing human somatic cells in a medium containing specific low molecular weight substances, wherein the human somatic cells are treated with an Oct4 protein before, during or after the culture.

The present invention is also directed to providing a composition for inducing OPCs from human somatic cells into which a nucleic acid molecule encoding an Oct4 protein is introduced or which are treated with Oct4 protein through direct reprogramming, the composition including a specific low molecular weight substance as an active ingredient.

The present invention is also directed to providing a method of differentiating the OPCs prepared by the above-described method into oligodendrocytes.

To achieve the above-described objects, the present invention provides a method of inducing OPCs from human somatic cells through direct reprogramming, the method including: culturing human somatic cells, into which a nucleic acid molecule encoding an Oct4 protein is introduced, in a medium containing (i) a TGF-β type I receptor inhibitor; (ii) an inhibitor of Rho-associated kinase (ROCK inhibitor); (iii) a histone deacetylase inhibitor; and (iv) a sonic hedgehog agonist (Shh agonist).

The present invention also provides a method of inducing OPCs from human somatic cells through direct reprogramming, which includes culturing human somatic cells in a medium containing (i) a TGF-β type I receptor inhibitor; (ii) an ROCK inhibitor; (iii) a histone deacetylase inhibitor; and (iv) a Shh agonist, wherein the human somatic cells are treated with the Oct4 protein before, during or after the culture.

The present invention also provides a composition for inducing OPCs from human somatic cells into which a nucleic acid molecule encoding an Oct4 protein is introduced or which are treated with Oct4 protein through direct reprogramming, the composition including (i) a TGF-β type I receptor inhibitor; (ii) a ROCK inhibitor; (iii) a histone deacetylase inhibitor; and (iv) a Shh agonist, as active ingredients.

The present invention also provides a method of differentiating OPCs into oligodendrocytes, the method including: culturing the OPCs prepared by the above-described method in a medium containing a ROCK inhibitor, a calcium channel agonist and a leukemia inhibitory factor (LIF).

DESCRIPTION OF SPECIFIC EMBODIMENTS OF THE INVENTION

Figure 1:
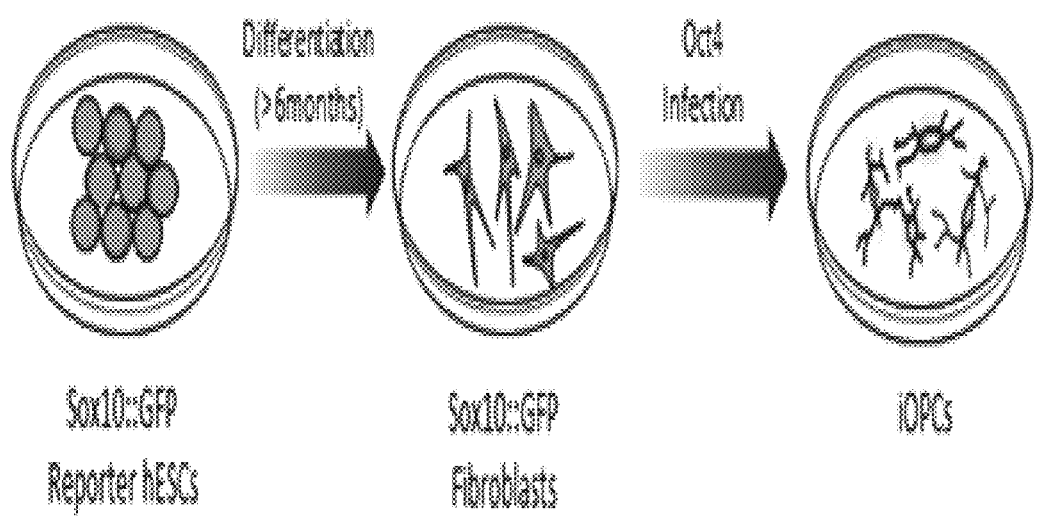
FIG. 1 shows the induction of iOPCs by introducing Oct4 into fibroblasts differentiated from Sox10::eGFP hESCs.

Unless defined otherwise, all of technical and scientific terms used in the specification have the same meanings as conventionally understood by those of ordinary skill in the art to which the present invention belongs. Generally, the nomenclature used herein is well known in the art and conventionally used.

In the present invention, it was confirmed that the induction of OPCs is possibly performed through the introduction of an Oct4 gene treated with various low molecular weight substances involved in the generation of oligodendrocytes after the overexpression of Oct4 in human somatic cells and the regulation of culture conditions, and also confirmed the expression of an OPC marker gene, epigenetic characteristics and the ability of myelination in vitro were also confirmed. In addition, it was confirmed that the OPCs induced thereby are differentiated and thus exhibited efficacy as a cell therapeutic agent.

The present invention relates to the development of a personalized cell therapeutic agent using a direct reprogramming method, and the inventors discovered a novel combination of substances on the basis of low molecular weight substances (KR 10-1357402) previously established, and established OPCs from human somatic cells by the combination with a gene without via neural stem cells.

In one exemplary embodiment of the present invention, following the introduction of an Oct4 gene to foreskin fibroblasts, which are human somatic cells, the cells were cultured in a medium containing A83-01, thiazovivin, valproic acid (VPA), purmorphamine and forskolin to confirm the expression of an OPC marker and then induction of OPCs from the human somatic cells was confirmed.

Therefore, in one aspect, the present invention relates to a method of inducing OPCs from human somatic cells through direct reprogramming, the method including: culturing human somatic cells, into which a nucleic acid molecule encoding an Oct4 protein is introduced, in a medium containing (i) a TGF-β type I receptor inhibitor; (ii) a ROCK inhibitor; (iii) a histone deacetylase inhibitor; and (iv) a Shh agonist.

In one exemplary embodiment of the present invention, although a nucleic acid-type gene encoding an Oct4 protein was introduced into foreskin fibroblasts, which are human somatic cells, to overexpress Oct4, for induction of OPCs, as well as the introduction of the Oct4 gene into the somatic cells, direct treatment of the somatic cells with the Oct4 protein may be used. The Oct4 protein may be treated before, during or after the somatic cells are cultured in a medium containing low molecular weight substances.

Therefore, in another aspect, the present invention relates to a method of inducing OPCs from human somatic cells through direct reprogramming, the method including: culturing the human somatic cells in a medium containing (i) a TGF-β type I receptor inhibitor; (ii) a ROCK inhibitor; (iii) a histone deacetylase inhibitor; and (iv) a Shh agonist, where the human somatic cells are treated with an Oct4 protein before, during or after the culture.

In the present invention, the medium may further contain a calcium channel agonist, or may further contain any one selected from the group consisting of RG108, BIX01294, SP600125, lysophosphatidic acid, Bayk8644, forskolin, dexamethasone, EX527 and rolipram, but the present invention is not limited thereto.

In the present invention, the TGF-β type I receptor inhibitor may be A83-01, the ROCK inhibitor may be thiazovivin, the histone deacetylase inhibitor may be valproic acid, the Shh agonist may be purmorphamine, and the calcium channel agonist may be forskolin, but the present invention is not limited thereto.

In the present invention, the "A83-01" is a transforming growth factor-β type I (TGF-β type I) receptor inhibitor, which is a substance that binds to a TGF-β type I receptor to interfere with a normal signaling process of TGF-β type I (Tojo M et al., Cancer Sci. 96: 791-800, 2005). TGF-β type I is a multifunctional peptide which performs various actions in cell proliferation and various types of cells, and such multifunctionality is known to play a critical role in the growth and differentiation of various types of tissue, for example, adipogenesis, myogenesis, bone cell formation, epithelial cell differentiation, and inhibits the proliferation of neural stem cells. In addition to the TGF-β type I receptor inhibitor A83-01, all of the TGF-β type I receptor inhibitors including SB432542 may be used, and the TGF-β type I receptor inhibitor A83-01 may be purchased commercially or prepared to be used as a low molecular weight substance, and the proliferation of neural stem cells is promoted by treatment with the inhibitor. The TGF-β type I receptor inhibitor A83-01 is added to the medium so as to be included at an effective concentration. The effective concentration may be influenced by parameters well known in the art, such as a medium type, a culture method, etc.

In the present invention, the "n-benzyl-[ 2-(pyrimidin-4-yl)amino]thiazole-4-carboxamide (thiazovivin)" is known to block an Rho/ROCK signal inducing apoptosis of neural cells and neural stem cells and a PTEN signal inhibiting proliferation of the neural stem cells, and expected to inhibit the apoptosis of the neural stem cells and increase a self-renewal activity and a self-proliferation activity (Matthias Groszer, et al., Science 294: 2186, 2001). Thiazovivin is a substance for selectively inhibiting a Rho-associated kinase (ROCK) by an ROCK inhibitor, and may employ Y-27632, etc., in addition to thiazovivin. Thiazovivin is added to a medium so as to be included at an effective concentration, and the effective concentration may be influenced by parameters well known in the art, such as a medium type, a culture method, etc.

In the present invention, the "2-propylpentaonic acid (VPA)" or "valproic acid (VPA)" is a substance which inhibits a histone deacetylase, and is known to exhibit a strong cytostatic anticancer activity by promoting the expression of cell proliferation inhibitory factors and genes necessary for inducing differentiation by forming chromatin in a high acetylated state to induce the differentiation of cancer cells and inhibit angiogenesis, and causing apoptosis of the cancer cells by fixing a cell cycle in the G1 state. A histone deacetylase (HDAC) inhibits gene transcription via pRB/E2F, and the breakdown in histone acetylation is involved in the generation of various types of cancer. The HDAC is highly expressed under severe environmental conditions such as hypoxia, hypoglycemia, cell carcinogenesis, etc. to promote cell proliferation by inhibiting the expression of cell proliferation inhibitory factors, and is known to be recognized as a key regulatory factor for cell carcinogenesis and differentiation regulation. Particularly, it is known that the VPA induces inositol reduction, inhibits GSK-30, activates an ERK pathway, and promotes PPAR activation. Trichostatin (TSA) or a derivative thereof as well as 2-propylpentanoic acid (VPA) may be used as the HDAC inhibitor, and the derivative includes various types of pharmaceutically acceptable inorganic salts or organic salts. When the treatment concentration is too low, there is less of an effect, and when the concentration is too high, it becomes toxic, and therefore, depending on a cell type, a suitable concentration should be determined.

In the present invention, the "purmorphamine" is a purine compound, and is known to be involved in a Shh signaling system. Purmorphamine is not particularly limited as long as a Shh signal may be induced, and various derivatives thereof may be used. For example, commercially available 2-(1-naphthoxy)-6-(4-morpholinoanilino)-9-cyclohexylpurin) may be used. Purmorphamine is added to a conventionally used medium to induce dedifferentiation into neural stem cell-like cells. In the treatment of purmorphamine, which is a Shh derivative, it is advantageous that it is not necessary to introduce a gene to produce neural stem cells from human fibroblasts. Purmorphamine is to be included at an effective concentration in the medium. The effective concentration of purmorphamine may be influenced by parameters well known in the art, such as a medium type and a culture method.

In the present invention, the "forskolin" used herein serves to increase an intracellular cAMP concentration by directly activating a catalytic subunit of adenylyl cyclase, and the "tranylcypromine" serves to inhibit monoamine oxidase (MAO), which is an enzyme that normally degrades norepinephrine at a nerve ending.

In the present invention, the culture medium includes all types of media conventionally used in neural stem cell culture, and the medium used in the culture generally includes a carbon source, a nitrogen source, and trace elements. The medium of the present invention may be a DMEM containing N2, B27, penicillin/streptomycin, non-essential amino acids, bFGF, PDGF and ascorbic acid, but the present invention is not limited thereto.

As the medium for induced cell culture in the present invention, a basic medium known in the art may be used without limitation. The basic medium may be prepared by artificial synthesis, or a commercially available medium may be used. Examples of the commercially available media may include, but are not limited to, a Dulbecco's modified Eagle's medium (DMEM), a minimal essential medium (MEM), basal medium eagle (BME), RPMI 1640, F-10, F-12, an α-minimal essential medium (α-MEM), a Glasgow's minimal essential medium (G-MEM), an Iscove's modified Dulbecco's medium, etc., and the medium is preferably DMEM. In an exemplary embodiment of the present invention, cells are cultured in DMEM.

In the present invention, the human somatic cells may be, but are not limited to, foreskin fibroblasts, hair-follicle dermal papillae, IMR90 lung fibroblasts or dermal fibroblasts. In addition, OPCs may also be induced from amniotic-derived stem cells or adipose-derived stem cells, rather than human somatic cells.

Oct4 of the present invention may be provided in the form of a protein or a nucleic acid encoding the protein, and an Oct4 protein of the present invention includes a protein having the amino acid sequence of the wild-type Oct4 protein, and a variant of the Oct4 protein.

The variant of the Oct4 protein refers to a protein having a different sequence due to deletion, insertion, and conservative or conservative substitution of one or more amino acid residues, or a combination thereof, from the natural amino acid sequence of Oct4. The variant may be a functional equivalent exhibiting the same biological activity as the natural protein or, if necessary, a variant with an enhanced structural stability with respect to a physical or chemical environment or an enhanced physiological activity by changing a physical or chemical property of the protein.

More preferably, the variant is a nucleic acid having the nucleotide sequence encoding the Oct4 protein, and the Oct4-encoding nucleotide sequence is a nucleotide sequence encoding a wild-type or variant-type Oct4 protein. The nucleotide sequence may be modified by substituting, deleting, inserting one or more bases, or a combination thereof, or may be naturally isolated or prepared by chemical synthesis. The nucleic acid having the nucleotide sequence encoding the Oct4 protein may be single stranded or a double stranded, and may be a DNA molecule (genome or cDNA) or an RNA molecule.

The nucleic acid encoding the Oct4 protein may be introduced into cells by a method known in the art, for example, using naked DNA in a vector form (Wolff et al. *Science*, 1990: Wolff et al. *J Cell Sci.* 103:1249-59, 1992), or using a liposome, a cationic polymer or the like. The liposome may be a phospholipid membrane prepared by mixing a cationic phospholipid such as DOTMA or DOTAP for gene introduction, and a nucleic acid-liposome complex is formed by mixing a cationic liposome and an anionic nucleic acid in a predetermined ratio.

The term "vector" used herein is an expression vector capable of expressing a desired protein in suitable host cells, and a gene construct including necessary regulatory elements that are operably linked to express a gene insert.

The term "operably linked" used herein refers to functional linkage between a nucleic acid expression regulatory sequence and a nucleic acid sequence encoding a desired protein to perform a general function. The operable linkage with a recombinant vector may be formed using a gene recombination technique well known in the art, and for site-specific DNA cleavage and linkage, enzymes generally well known in the art may be used.

The vector of the present invention may include a signal sequence or leader sequence for membrane targeting or secretion, as well as expression regulatory elements such as a promoter, an operator, an initiation codon, a termination codon, a polyadenylation signal and an enhancer, and may be prepared in various forms according to purpose. The promoter for the vector may be constitutive or inducible. Also, the expression vector may include a selectable marker for selecting host cells containing a vector, and a replicable expression vector includes a replication origin. The vector may be self-replicated or integrated into host DNA.

Such a vector may be a plasmid vector, a cosmid vector or a viral vector, and preferably, a viral vector. The viral vector may be, but is not limited to, a vector derived from a human immunodeficiency virus (HIV), a murine leukemia virus (MLV), an avian sarcoma leukosis virus (ASLV), a spleen necrosis virus (SNV), a Rous sarcoma virus (RSV) or a mouse mammary tumor virus (MMTV), an adenovirus, an adeno-associated virus, or a herpes simplex virus.

In the present invention, the OPCs may express any one or more markers selected from the group consisting of PDGFRα, A2B5, Olig2, Sox10, S100b and ZFP536, and may not express Sox1, Sox2 and Pax6 markers.

In still another aspect, the present invention relates to a composition for inducing OPCs from human somatic cells into which a nucleic acid molecule encoding an Oct4 protein is introduced or which are treated with Oct4 protein through direct reprogramming, which includes (i) a TGF-β type I receptor inhibitor; (ii) a ROCK inhibitor; (iii) a histone deacetylase inhibitor; and (iv) a Shh agonist, as active ingredients.

In the present invention, the composition may further contain a calcium channel agonist, and further contain any one selected from the group consisting of RG108, BIX01294, SP600125, lysophosphatidic acid, Bayk8644, forskolin, dexamethasone, EX527 and rolipram.

In the present invention, the TGF-β type I receptor inhibitor may be A83-01, the ROCK inhibitor may be thiazovivin, the histone deacetylase inhibitor may be valproic acid, the Shh agonist may be purmorphamine, and the calcium channel agonist may be forskolin, but the present invention is not limited thereto.

In the present invention, the OPCs may not express the Sox1, Sox2 and Pax6 markers.

In another exemplary embodiment of the present invention, it was confirmed that induced OPCs differentiate into oligodendrocytes using a differentiation medium containing triiodo-1-thyronine (T3), thiazovivin, forskolin and LIF, after a growth factor and a specific low molecular weight substance are removed from a conventional induction medium.

Accordingly, in yet another aspect, the present invention relates to a method of differentiating OPCs into oligodendrocytes, which includes culturing the OPCs prepared by the above-described method in a medium containing a ROCK inhibitor, a calcium channel agonist and LIF.

In the present invention, the medium may be DMEM containing N2, B27, penicillin/streptomycin, non-essential amino acids, ascorbic acid and T3, but the present invention is not limited thereto.

In the case of the OPCs of the present invention which are known as cells that are present in an extremely small amount in the cerebrum, there is a low differentiation rate in neural stem cells constituting the cerebrum, and thus there are many difficulties in establishing the OPCs from upper stem cells. Therefore, in the conventional art, while various studies are being conducted to efficiently establish the OPCs, the OPCs can be established through long-term differentiation for at least 70 days.

The present invention may solve such a problem with a high cell conversion rate in a short period, since the OPCs may be established in a relatively short culturing period such as approximately 1 to 2 weeks through direct reprogramming, that is, without via neural stem cells. In addition, since there is still no report on the establishment of the OPCs through direct reprogramming using human somatic cells, demyelinating disease-associated therapeutic agents are expected to be useful in the future cell therapeutic agent market, and the low molecular weight substance of the present invention is expected to play a critical role in treating the nervous system.

A demyelinating disease is an intractable neurological disease occurring due to the absence of oligodendrocytes, and in the conventional art, most studies focus on treating neurological diseases by establishing the OPCs from embryonic stem cells. However, there is difficulty in establishing the embryonic stem cells as therapeutic agents because there is an ethical problem as well as a limit due to immune rejection. Therefore, the method of establishing the OPCs from somatic cells according to the present invention through direct reprogramming may solve the ethical problem, and since there is no immune rejection, can also highly contribute to the establishment of personalized cell therapeutic agents.

EXAMPLES

Hereinafter, the present application will be described in further detail with reference to examples. The examples are merely provided to more fully describe the present application, and it will be obvious to those of ordinary skill in the art that the scope of the present application is not limited to the following examples.

Example 1: Selection of Low Molecular Weight Substance and Establishment of Induction Conditions 1-1: Selection of Low Molecular Weight Substance Using Sox10 Reporter System The inventors have established conditions capable of inducing neural stem cells from mouse cells only with a low molecular weight substance without gene introduction (KR 10-1357402). Accordingly, to establish new conditions capable of inducing human somatic cells into OPCs on the basis of the low molecular weight substance that had been established in the previous study, a low molecular weight substance was selected using a Sox10 reporter system (Sox10::eGFP), which is a gene known to be important in development of oligodendrocytes (FIG. 1).

When Oct4 gene-introduced cells were cultured in a reprogramming medium (RM: DMEM with high Glucose+ 5% knock out serum replacement (KSR)+1% penicillin/ streptomycin+1% non-essential amino acids+20 ng/ml basic FGF (bFGF)+20 ng/ml human recombinant platelet derived growth factor (PDGF)+50 µg/ml ascorbic acid), one week after induction, it was confirmed that a cell length was shorter and a cell size was smaller through mesenchymal to epithelial transition (MET), thereby forming an epithelial-like colony. These cells are subcultured in a Matrigel-coated dish, and selected from a medium containing A83-01, thiazovivin, valproic acid and purmorphamine, which is a combination of low molecular weight substances that can induce neural stem cells (DMEM with high glucose+1×N2+ 1×B27 (without vitamin A)+1% penicillin/streptomycin+1% non-essential amino acids+basic 20 ng/ml FGF (bFGF)+20 ng/ml human recombinant platelet-derived growth factor (PDGF)+50 µg/ml ascorbic acid+0.5 µM A83-01+0.5 µM thiazovivin+0.1 mM valproic acid (VPA)+0.5 µM purmorphamine) by additionally combining an epigenetic modulator and low molecular weight substances influencing the development of the nervous system.

Figure 3:
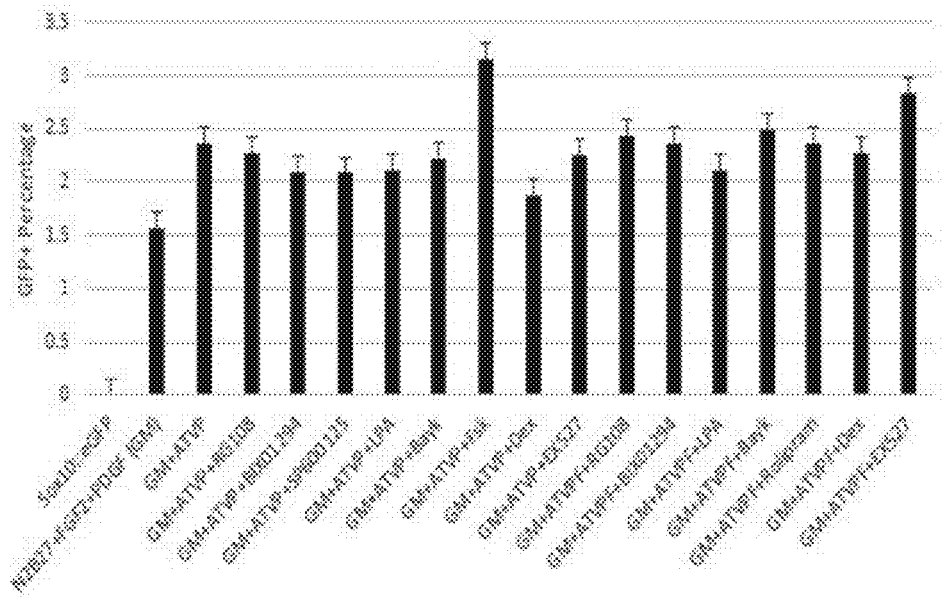
FIG. 3 shows an FACS analysis result for GFP+ distribution after Oct4-introduced Sox10::eGFP fibroblasts are treated with a low molecular weight substance.
Figure 3:
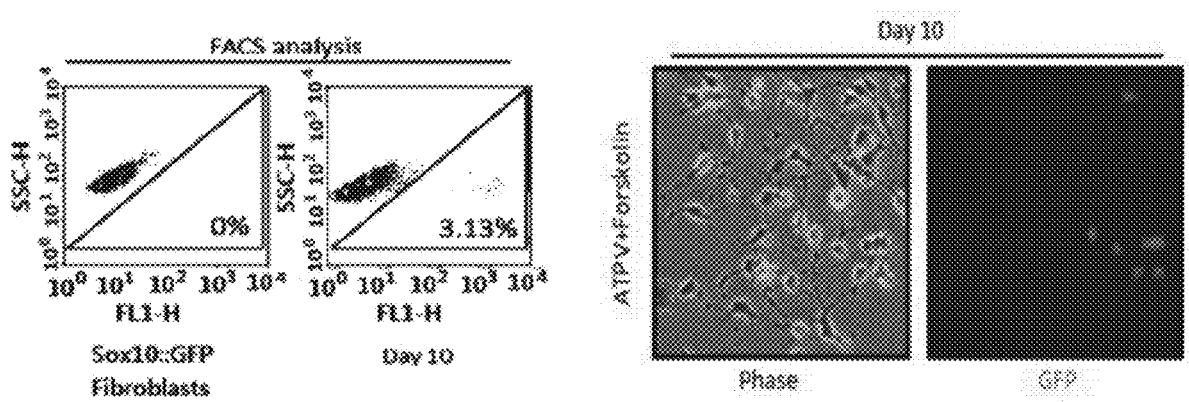
Figure 4:
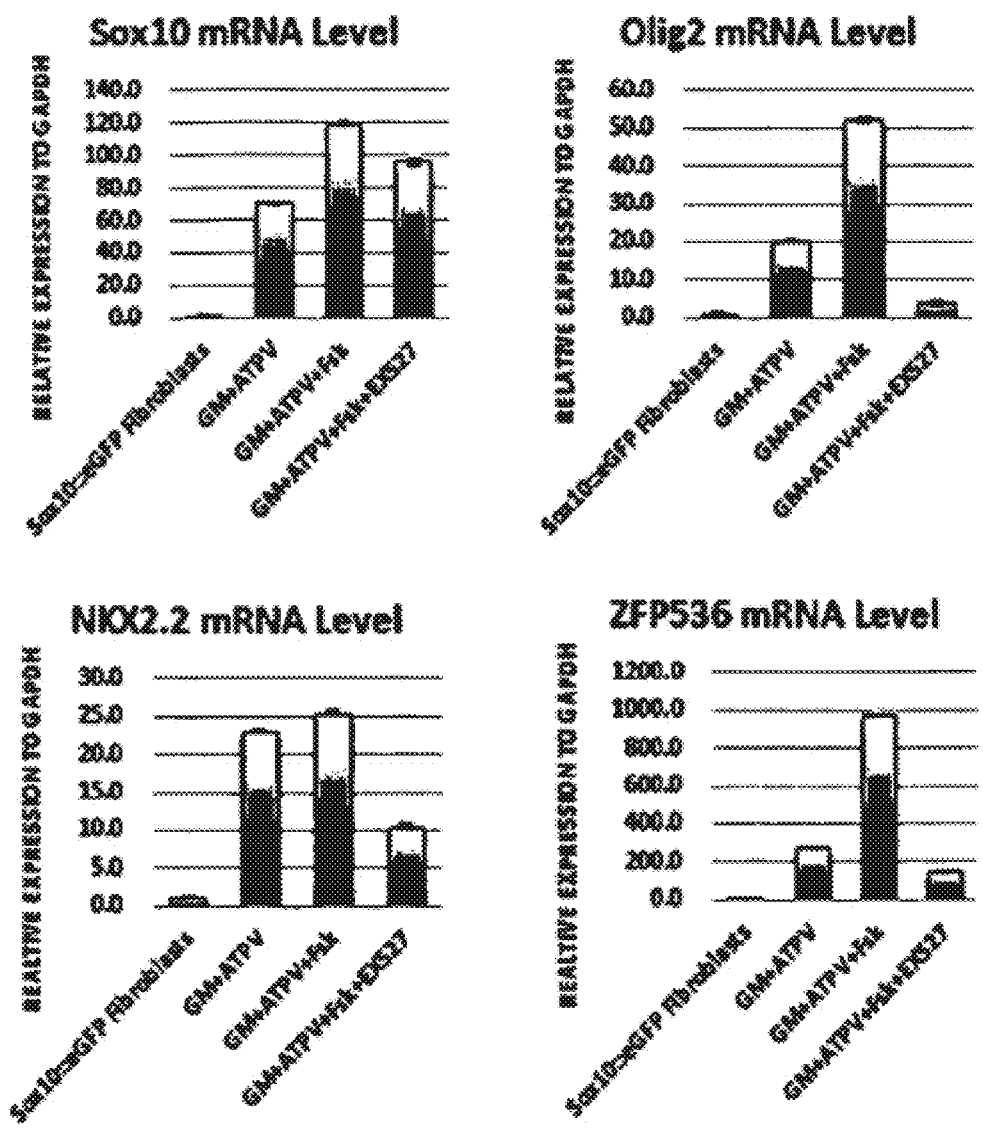
FIG. 4 shows a real-time PCR result for mRNA levels of Olig2, NKX2.2 and ZFP536 which are known as markers for OPCs, excluding Sox10, after Oct4-introduced Sox10::eGFP fibroblasts are treated with a low molecular weight substance.

The conditions for combining low molecular weight substances are as follows:

ATVP: 0.5 µM A83-01+0.5 µM thiazovivin+0.1 mM valproic acid (VPA)+0.5 µM purmorphamine, RG108: 0.5 µM RG108, BIX01294: 0.25 µM BIX01294, SP600125: 2 µM SP600125, LPA: 2 µM lysophosphatidic acid, Bayk: 2 µM Bayk8644, Fsk: 10 µM forskolin, Dex: 1 µM dexamethasone, EX527: 5 µM EX527, Rolipram: 2 µM rolipram As a result, FACS analysis showed that Sox10::eGFP was most highly expressed (3.31%) under the 10 µM forskolin-addition condition (FIG. 3), and real-time PCR showed that the highest mRNA expression of Olig2, NKX2.2 and ZFP536, which were known as markers for the OPCs, as well as Sox10 was also exhibited under the condition (FIG. 4).

1-2: Establishment of KSR-excluded induction conditions

There is a report that it is possible to perform conversion to neural stem cells when knockout serum replacement (KSR) contained in the reprogramming medium (RM) of Example 1-1 is used with Oct4 overexpression.

Figure 5:
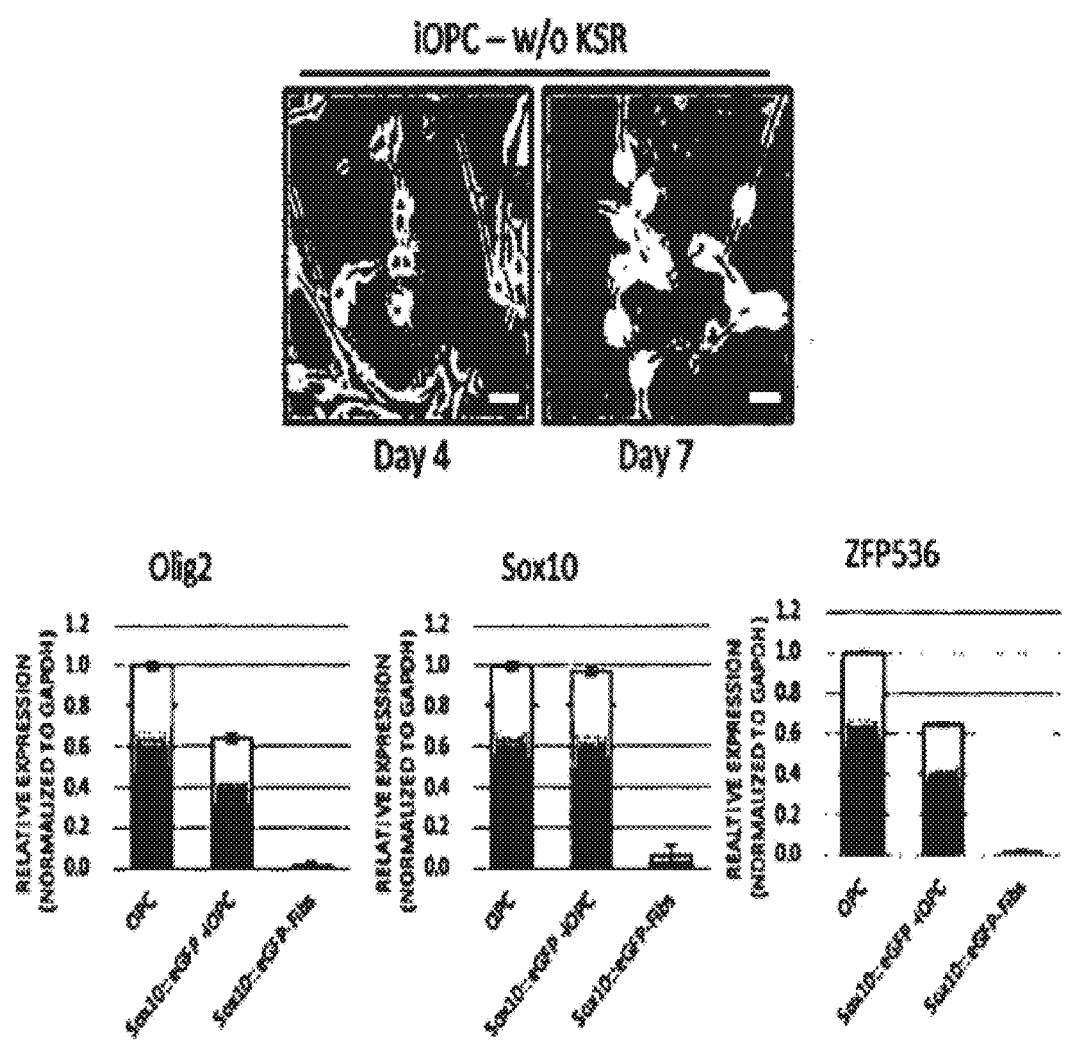
FIG. 5 shows the expression of Olig2, Sox10 and ZFP536 markers, and the morphology of OPCs induced from human somatic cells without using knockout serum replacement (KSR).

Therefore, as a result of inducing the OPCs under KSR-excluded conditions to exclude OPCs induced by differentiation, rather than reprogramming, it was confirmed that the morphology of the OPCs appeared, and the expression of Olig2, Sox10 and ZFP536, which are markers for the OPCs, was confirmed by PCR (FIG. 5).

Figure 6:
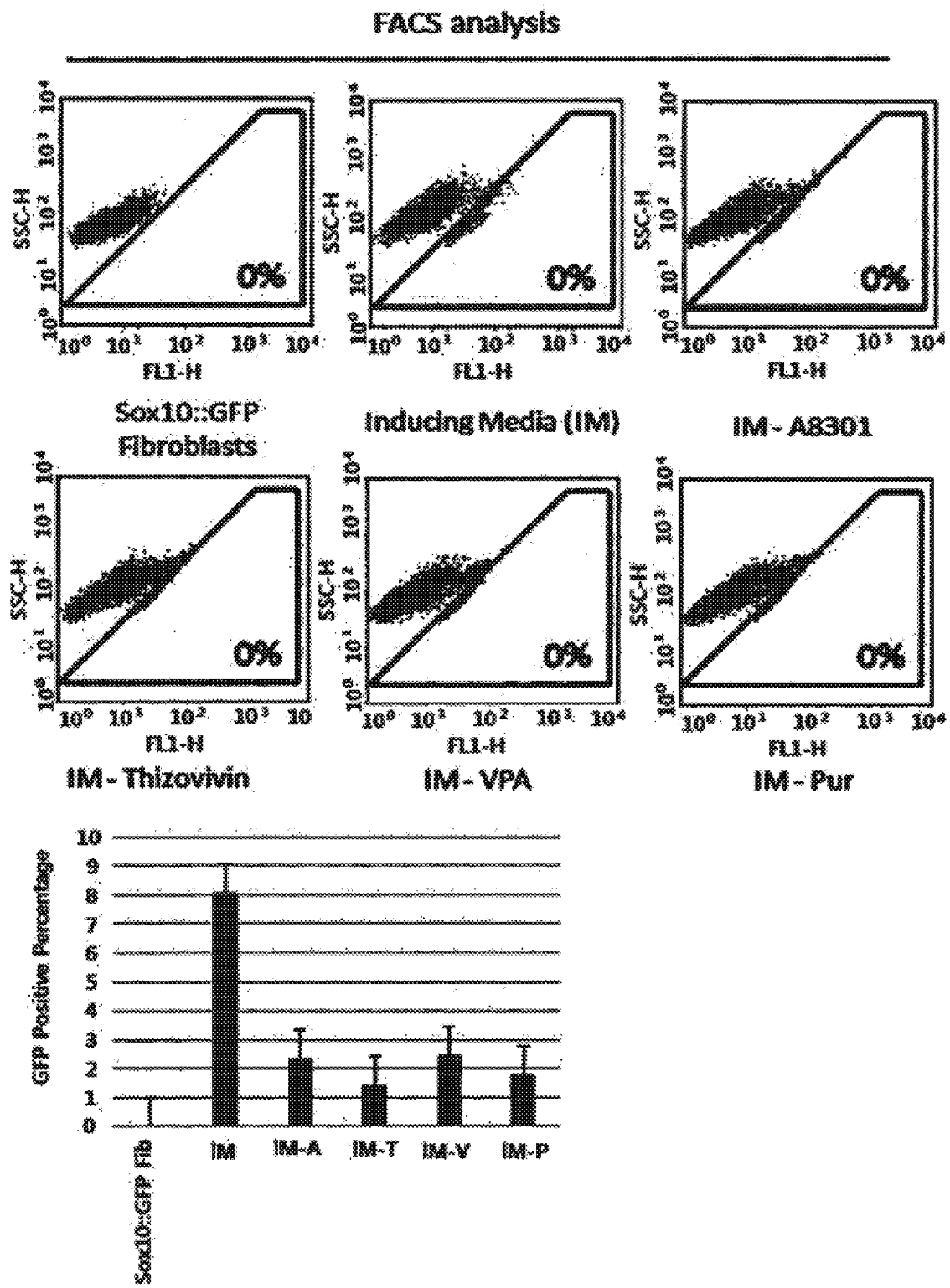
FIG. 6 shows the comparison of Sox10 expression in a medium from which low molecular weight substances are removed one by one, and in a medium containing all of the low molecular weight substances.

In addition, as a result of removing the treated low molecular weight substances one by one under the induction conditions of Example 1-1 to select the optimum combination of low molecular weight substances, it was confirmed that the highest Sox10 expression was observed in a medium containing all of the low molecular weight substances (FIG. 6).

Figure 2:
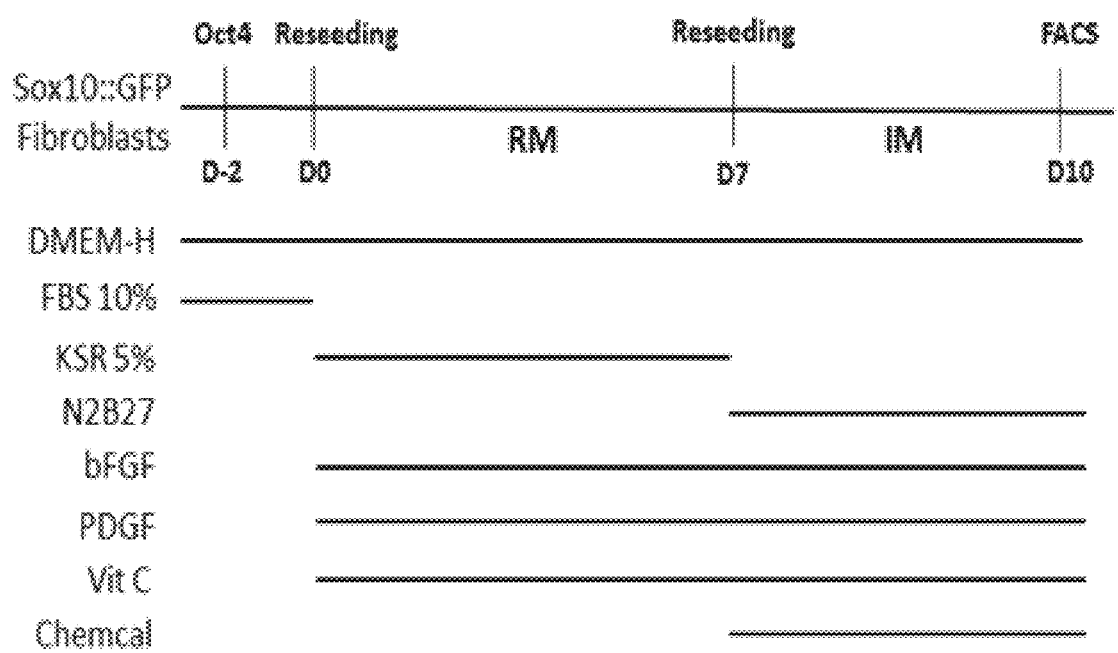
FIG. 2 shows the process of selecting a low molecular weight substance necessary to establish induced OPCs (iOPCs) through culture in inducting media (IM) after Oct4-introduced Sox10::eGFP fibroblasts are cultured in reprogramming media (RM) for 7 days.

Therefore, the established conditions (IM: DMEM with high glucose+1×N2+1×B27 (without vitamin A)+1% penicillin/streptomycin+1% non-essential amino acids+20 ng/ml basic FGF (bFGF)+20 ng/ml human recombinant platelet-derived growth factor (PDGF)+50 m/ml ascorbic acid+0.5 µM A83-01+0.5 µM thiazovivin+250 µM valproic acid (VPA)+0.5 µM purmorphamine+10 µM forskolin) were determined as induction conditions for the OPCs (FIG. 2).

Example 2: Induction and Confirmation of OPCs from Human Somatic Cells

Figure 7:
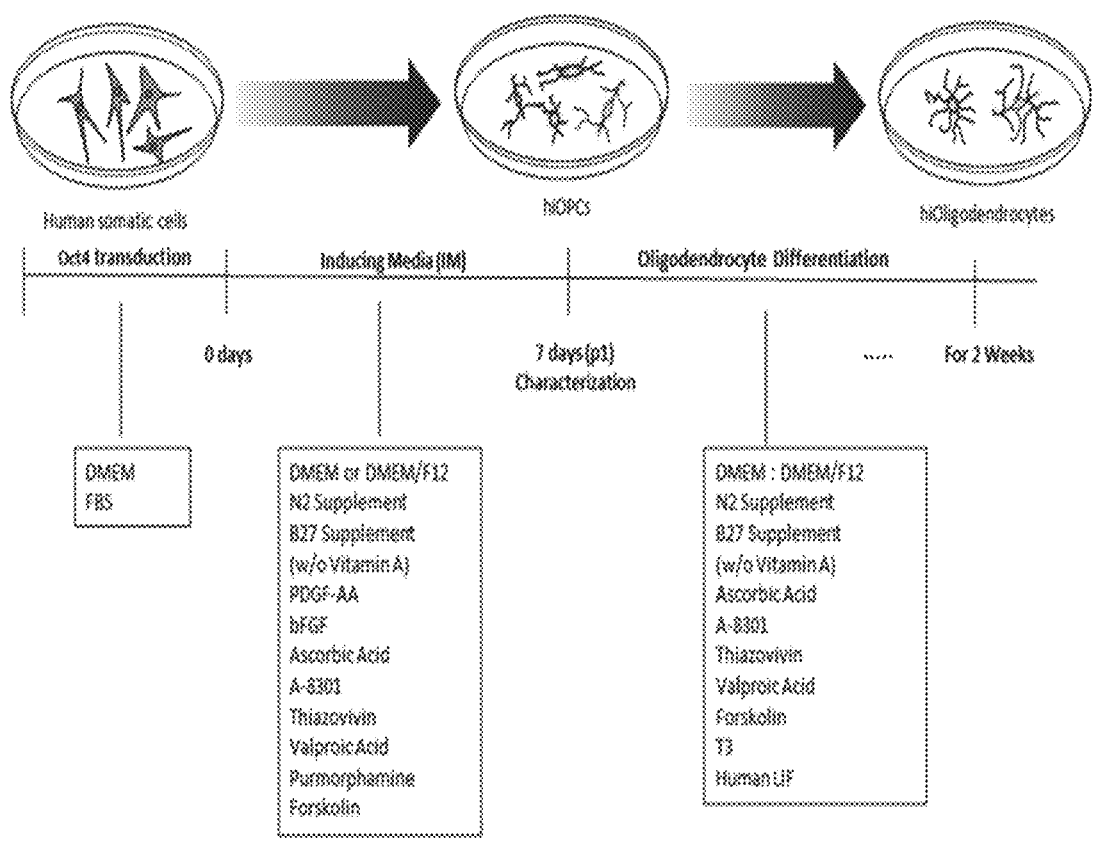
FIG. 7 shows the induction of iOPCs from human somatic cells without using KSR.

Since the Sox10::eGFP fibroblasts used as the reporter cell line of Example 1-1 are cells obtained through differentiation from embryonic stem cells (ES cells), other stem cells, excluding fibroblasts, may not be completely excluded, and thus it may not be seen as direct reprogramming from somatic cells. In addition, since a KSR-containing medium was used in the establishment of neural stem cells after Oct4 was overexpressed in human somatic cells by Shengding and Mickie Bhatia research teams in the United States, in this Example, to induce direct reprogramming from human somatic cells which are not derived from embryos without via neural stem cells, which are upper stem cells of the OPCs, a KSR-containing reprogramming medium (RM) was not used (FIG. 7).

Figure 8:
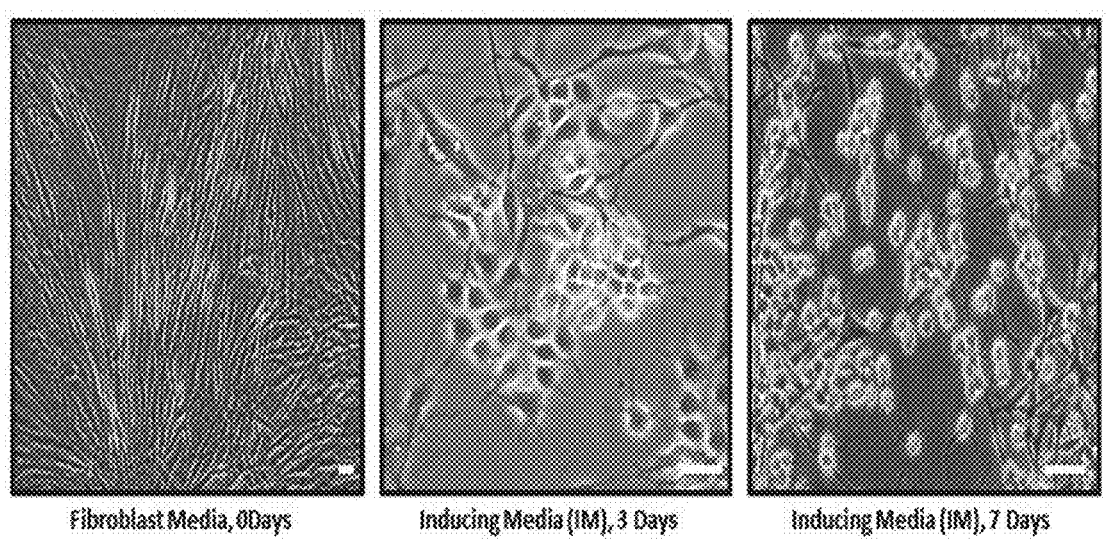
FIG. 8 shows cells undergoing mesenchymal to epithelial transition (MMET) three days after culturing in an inducting medium (IM), and cells with a similar morphology to OPCs 7 days after culturing.

That is, as a result of introducing an Oct4 gene into BJ cells, subculturing in a Matrigel-coated dish, and culturing for 4 days under induction conditions (IM) for the OPCs established in Example 1-2, cells having undergone MET were observed, and 7 days after culturing, cells that look like oligodendrocytes were observed (FIG. 8).

Figure 9:
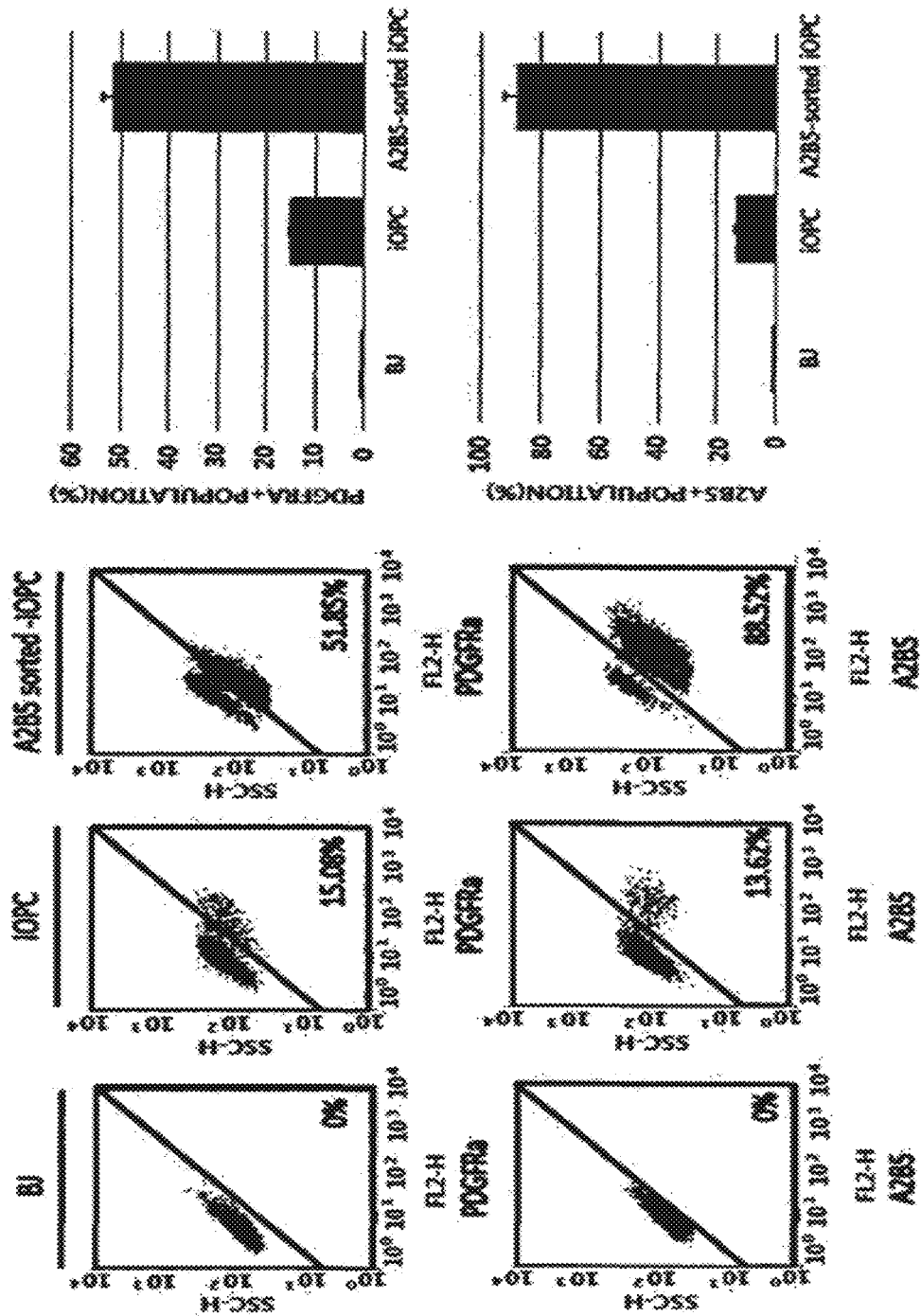
FIG. 9 shows the expression of PDGFRα and A2B5, which are OPC markers in iPOCs, through FACS analysis.
Figure 10:
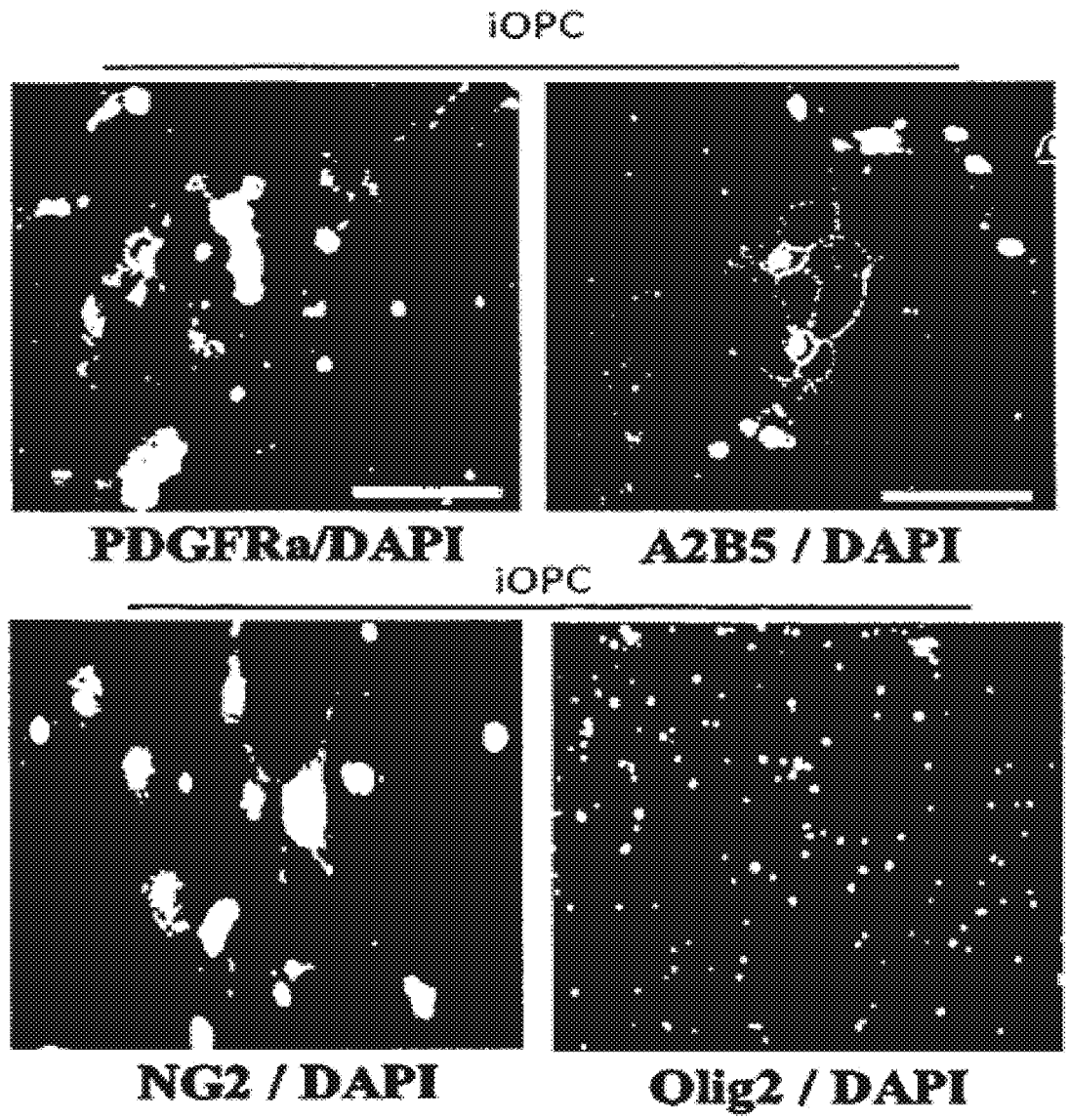
FIG. 10 shows the expression of PDGFRα and A2B5, in iPOCs, in the cell membrane, which is identified by immunohistochemical staining.
Figure 11:
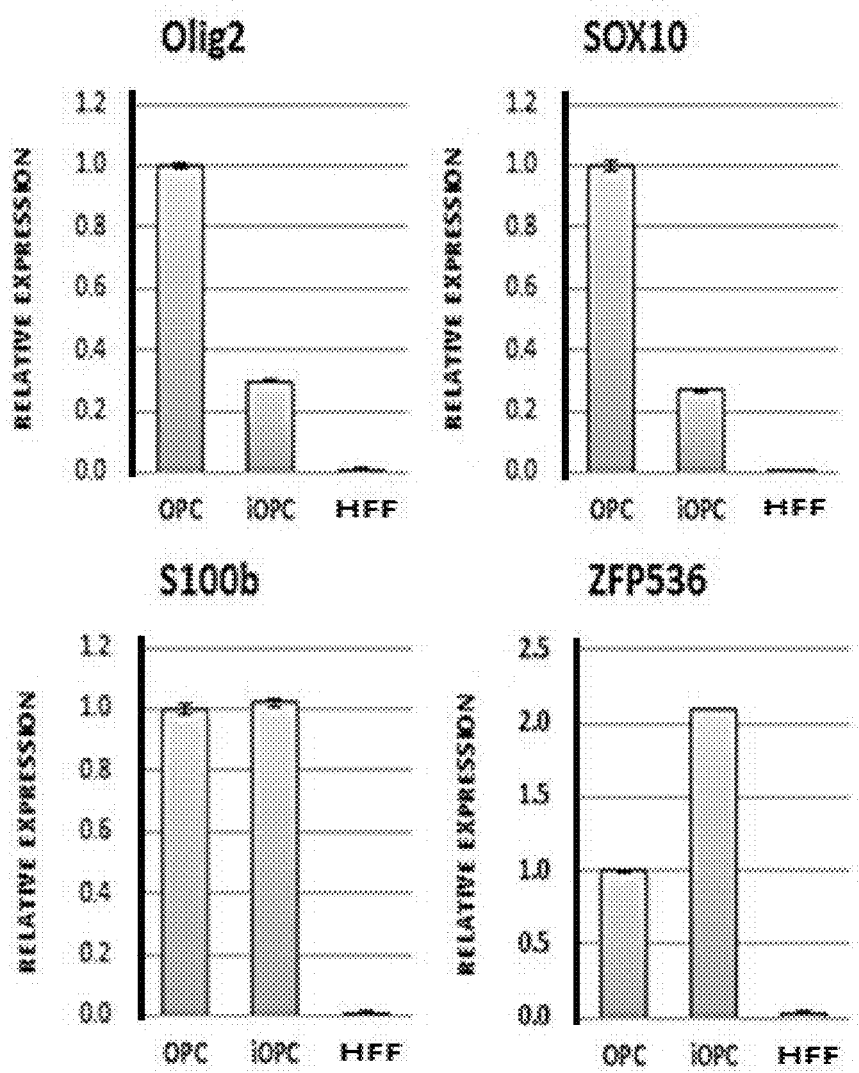
FIG. 11 shows comparative analysis of mRNA expression of OPC marker genes in iPOCs through real-time PCR.

In addition, 7 days after culturing, to check whether the cells are OPCs, FACS analysis (FIG. 9) and immunohistochemical staining (FIG. 10) showed that representative markers for the OPCs, such as PDGFRα and A2B5, were expressed in approximately 10% of the cells, and real-time PCR showed that markers expressed in OPCs derived from dedifferentiated stem cells, such as Olig2, Sox10, S100b and ZFP536, were expressed in the induced OPCs (FIG. 11).

On the basis of the above result, the established cells were named iOPCs.

Example 3: Differentiation of OPCs into Oligodendrocytes 3-1: Differentiation into Oligodendrocytes To confirm an ability to differentiate OPCs induced in Example 2 into oligodendrocytes, a growth factor was removed from a conventional medium, and the medium was replaced with a differentiation medium (DMEM with high glucose+1×N2+1×B27 (without vitamin A)+1% penicillin/streptomycin+1% non-essential amino acids+50 μg/ml ascorbic acid+40 ng/ml T3 (triiodo-1-thyronine)+0.5 μM thiazovivin+10 μM forskolin+10 ng/ml human leukemia inhibitor factor (LIF)).

Figure 12:
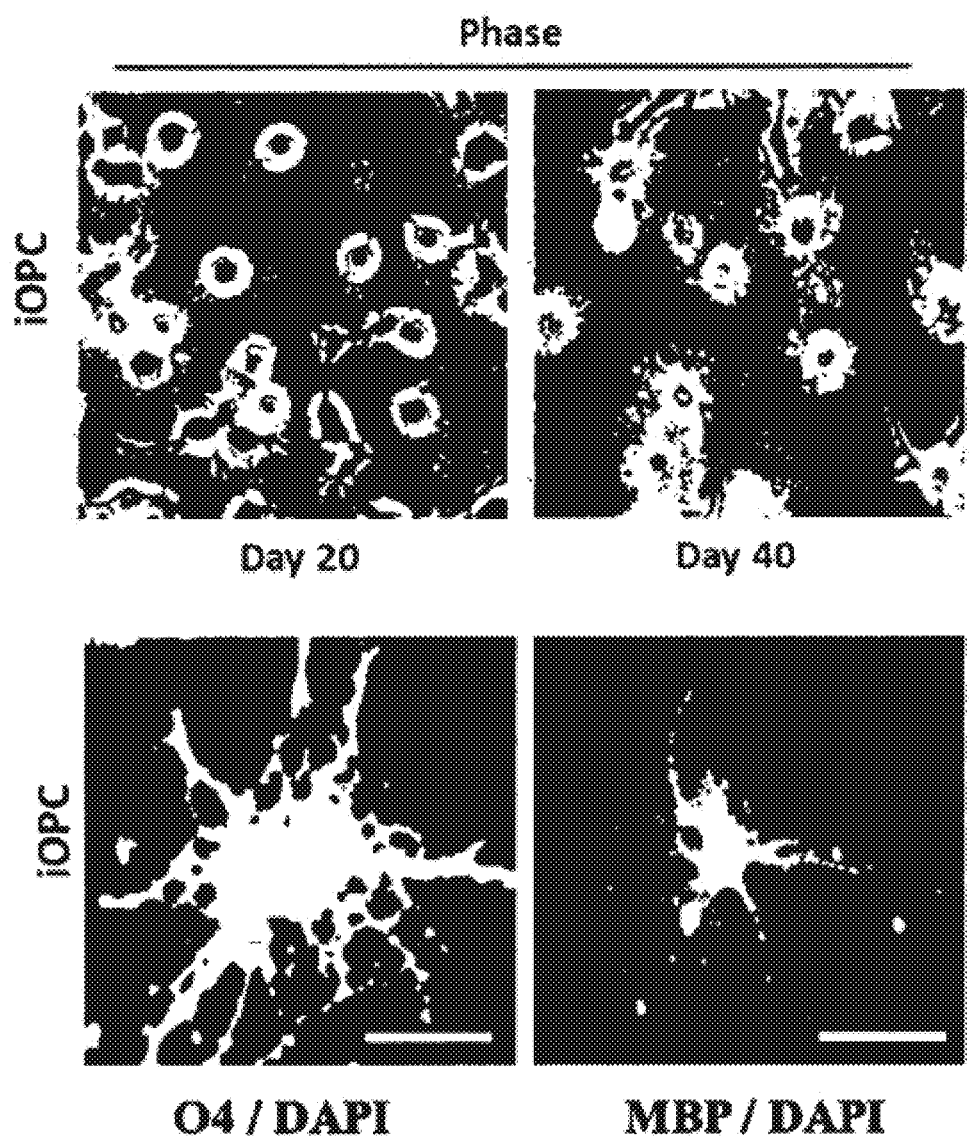
FIG. 12 shows the differentiation of oligodendrocytes in a typical branch type shown when established iOPCs are cultured for 40 to 60 days under differentiation conditions in which growth factors are excluded, and an increase in the expression of markers for oligodendrocytes, such as MBP and MAG, confirmed through real-time PCR and immunohistochemical staining.

As a result, a typical branch-type morphology of the oligodendrocyte was shown, and real-time PCR showed that MBP and MAG expression increased (FIG. 12).

Figure 13:
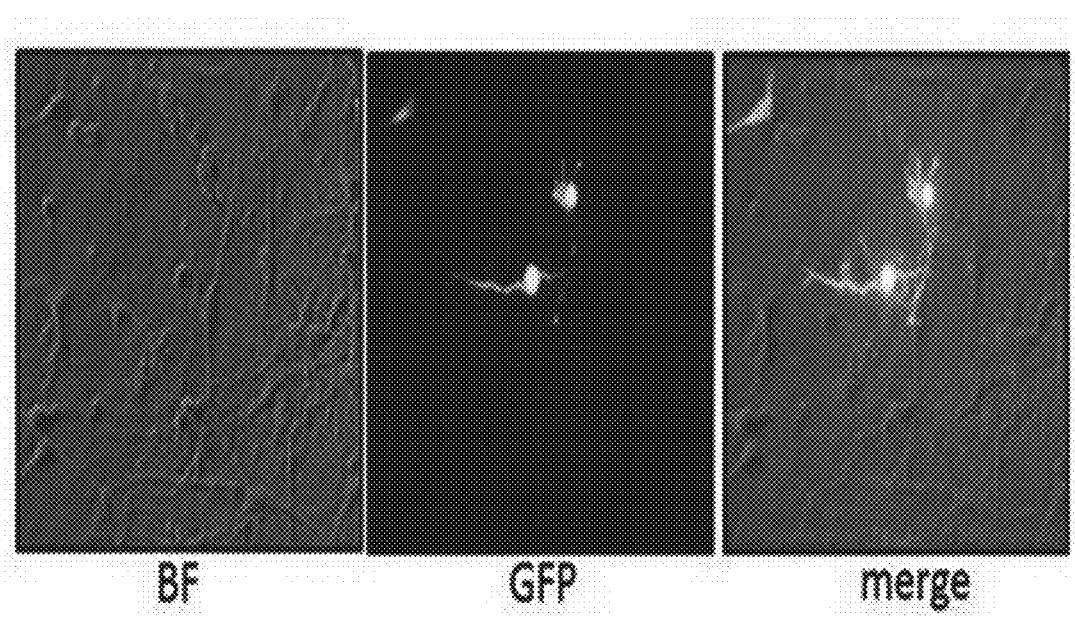
FIG. 13 shows that iOPCs expressing GFP are co-cultured with mouse neurons and differentiate into oligodendrocytes, and then myelinated with the neurons.

In addition, as a result of co-culturing with neurons obtained from the hippocampus of a rat to confirm in vitro myelination by differentiated oligodendrocytes, it was confirmed that the neurons were myelinated by the differentiated oligodendrocytes (FIG. 13).

3-2: Confirmation of In Vivo Differentiation Activity and Therapeutic Activity

To confirm in vivo differentiation activity and therapeutic activity of OPCs as a cell therapeutic agent, the OPCs induced in Example 2 were transplanted into multiple sclerosis animal models (experimental autoimmune encephalomyelitis mouse model (EAE mouse model)).

Figure 14:
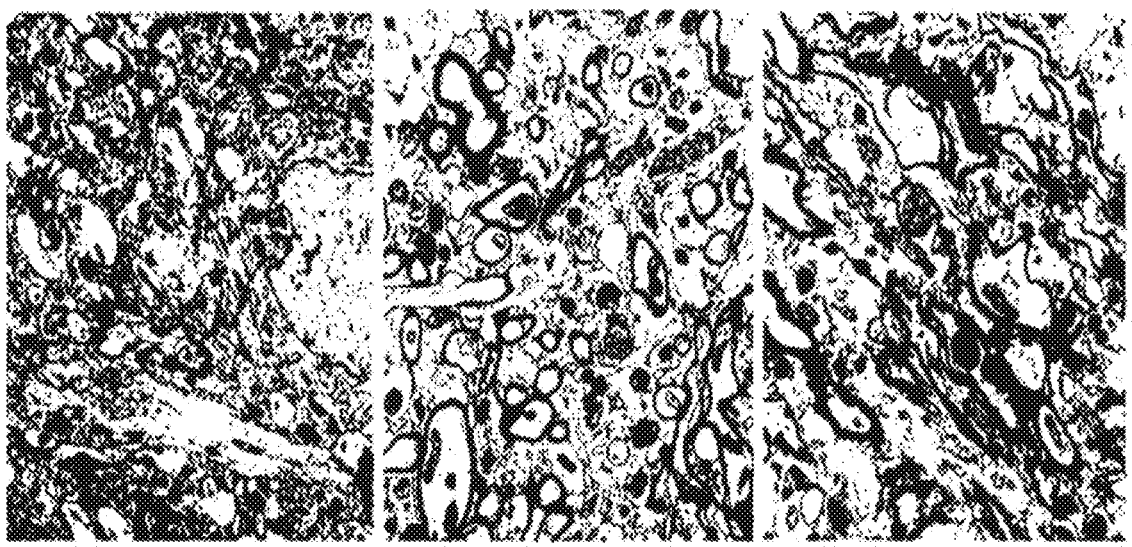
FIG. 14 shows myelin obtained after iOPCs are transplanted into a multiple sclerosis animal model, to test in vivo differentiation and efficacy as a therapeutic agent, is similar to that of a normal rat.

As a result, it was confirmed that, while no myelin was shown in a PBS-injected control, in an iOPC-transplanted group, myelin similar to that in a normal mouse were observed (FIG. 14). In other words, it can be seen that the iOPCs were differentiated in vivo and thus exhibited efficacy as a cell therapeutic agent.

Example 4: Induction of OPCs Through Direct Reprogramming

In this Example, to confirm that iOPCs were established through direct reprogramming, rather than differentiated from neural stem cells induced after Oct4 overexpression during the establishment of iOPCs, a change in gene expression during 7 days of induction was confirmed by real-time PCR.

Figure 15:
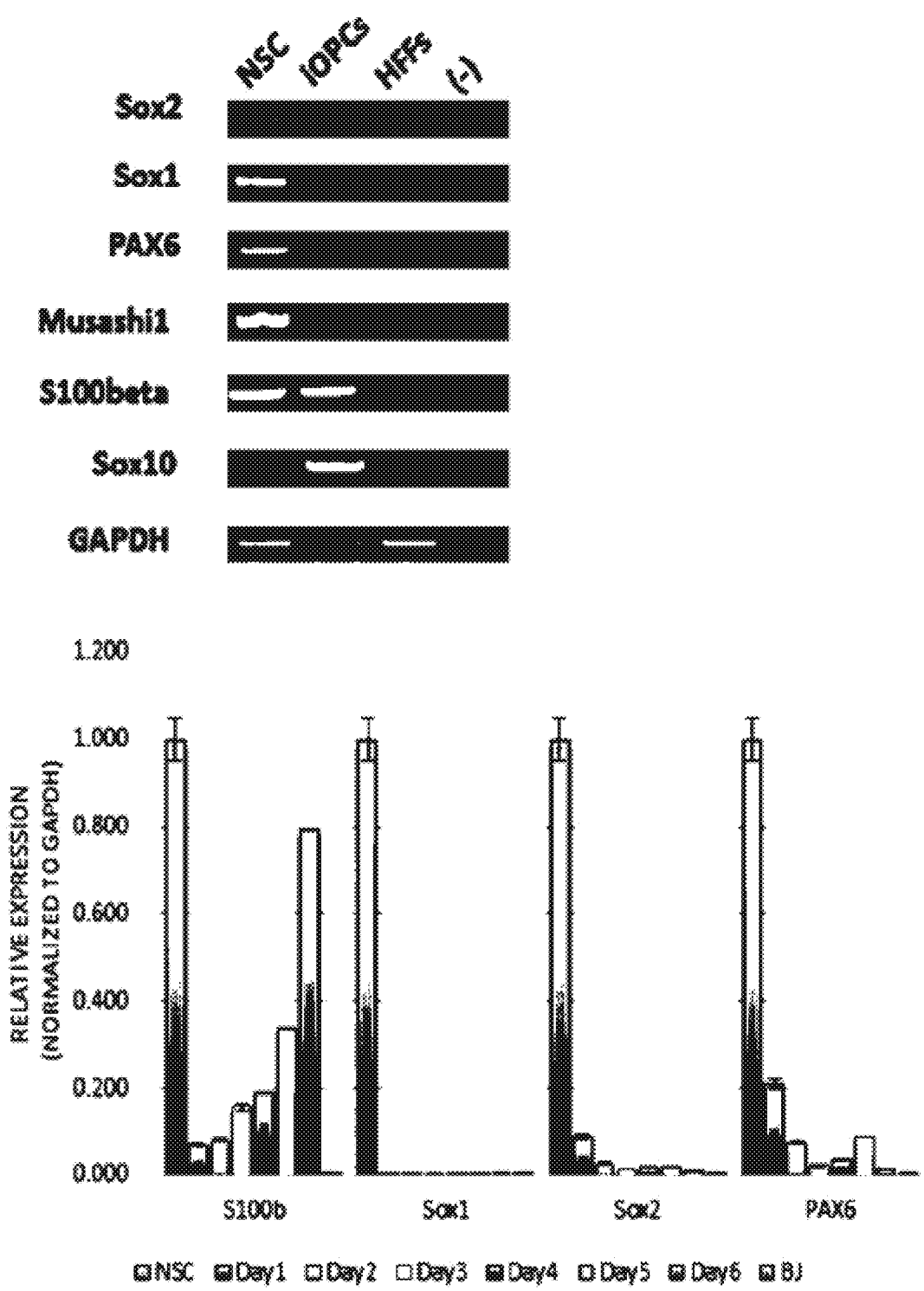
FIG. 15 shows the expression of neural stem cell markers such as Sox1, Sox2, and Pax6 genes during an induction period, confirmed through real-time PCR to prove that iOPC induction is not achieved by differentiation via neural stem cells after Oct4 overexpression.

As a result, it was confirmed that all of the Sox1, Sox2 and Pax6, which were known as the markers for the neural stem cells, were not expressed for 7 days (FIG. 15).

Figure 16:
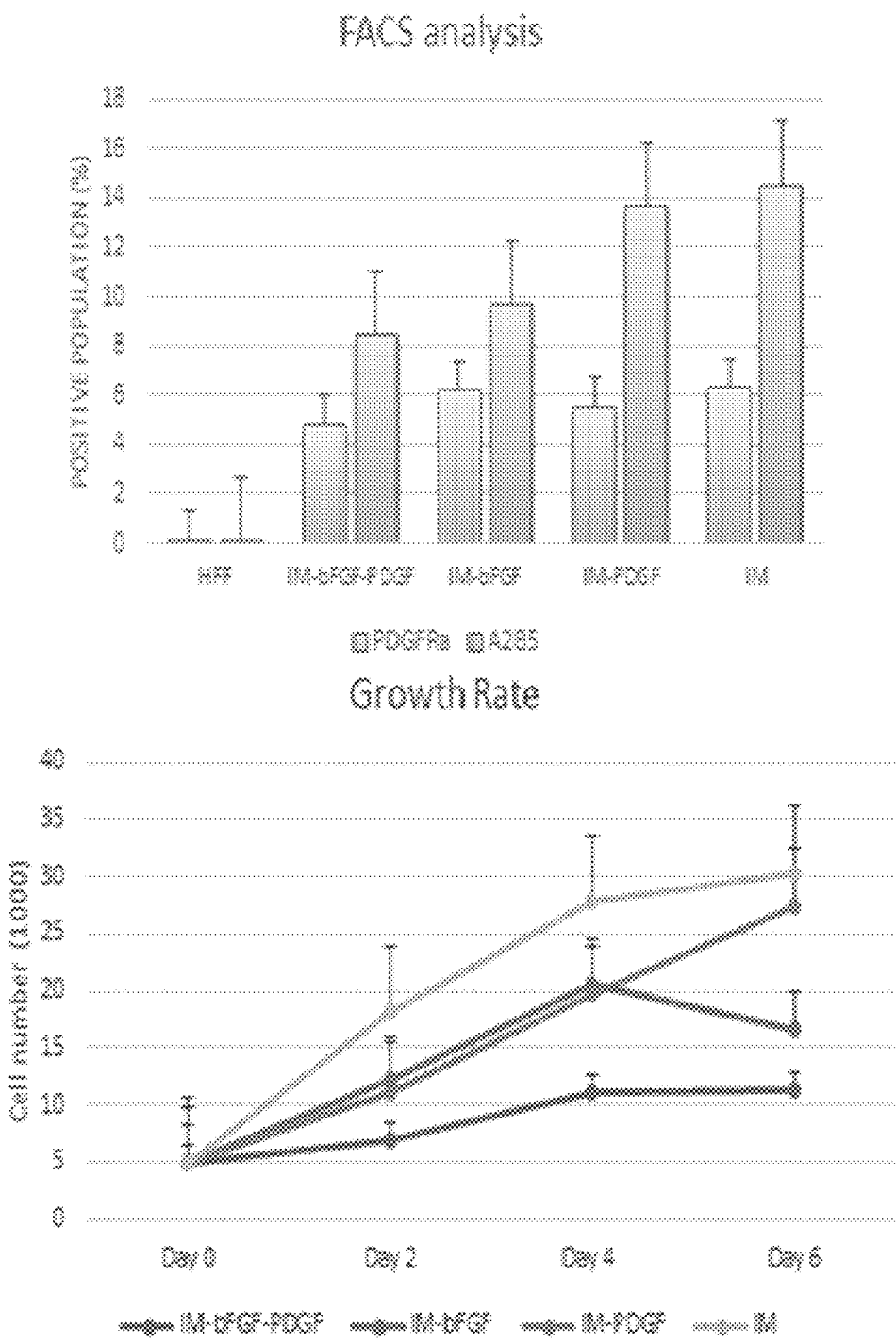
FIG. 16 shows proliferation after growth factors of OPCs, such as bFGF and PDGF-AA, are removed from a culture solution during induction, to prove that iOPC induction is not achieved via neural stem cells, and iOPCs are proliferated by a reaction with the growth factors, and the expression of OPC markers such as PDGFRα and A2B5 in the growth factor-dependent proliferated cells, confirmed by FACS analysis.

In addition, it was observed that cells were proliferated by FGF2 and PDGF-AA, which were known as growth factors for the OPCs, during 7 days of induction, and FACS analysis showed that the proliferated cells are cells exhibiting PDGFRα and A2B5 (FIG. 16).

Therefore, based on the above result, it can be proved that iOPCs established OPCs through direct reprogramming without via neural stem cells, during 7 days of induction.

Example 5: Induction of OPCs from Various Human Somatic Cells

To confirm whether the induction into OPCs is possibly performed in other human somatic cells as well as the foreskin fibroblasts, five different types of cells (hair-follicle dermal papillae, amniotic-derived stem cells, IMR90 lung fibroblasts, dermal fibroblasts and adipose-derived stem cells), in which Oct4 was overexpressed, were induced into OPCs.

Figure 17:
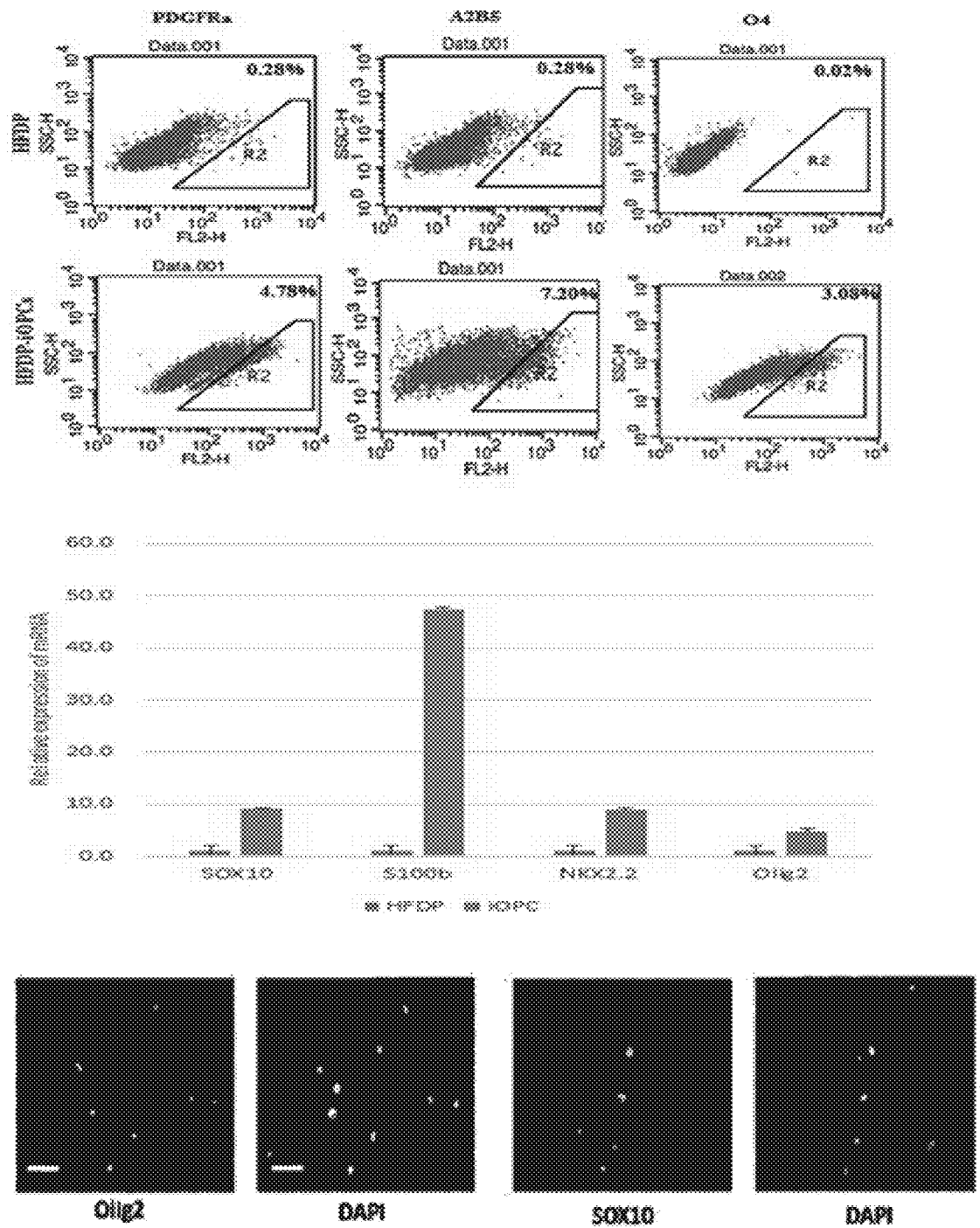
FIG. 17 shows the expression of OPC markers after Oct4-overexpressing hair follicle dermal papillae are cultured in IM, which is analyzed by FACS analysis, real-time PCR and immunohistochemical staining.
Figure 18:
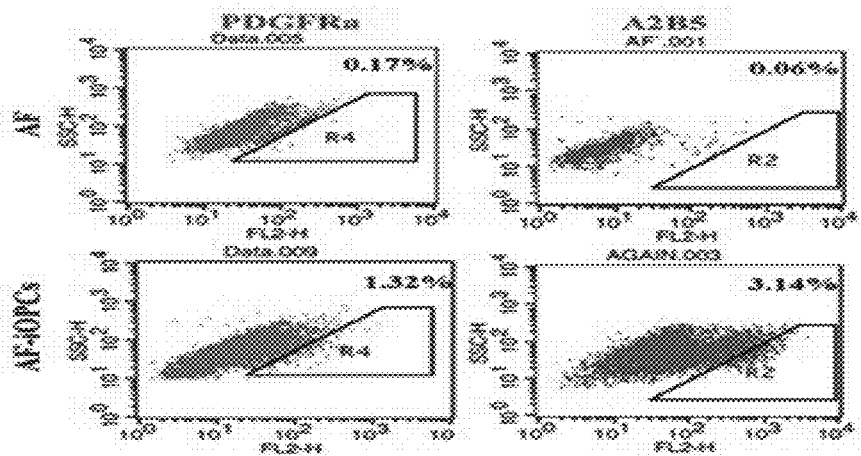
FIG. 18 shows the expression of OPC markers after Oct4 is overexpressed in amniotic fluid stem cells, adipose-derived stem cells in various age ranges and dermal cells, and cultured in IM, which is analyzed by real-time PCR or FACS analysis.
Figure 18:
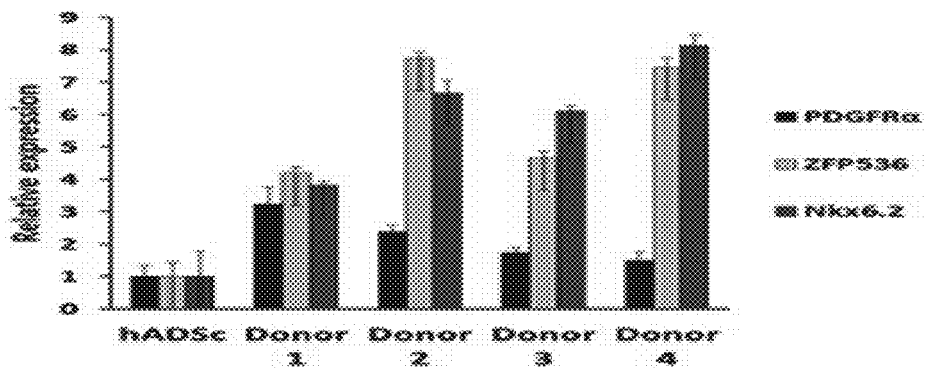
Figure 18:
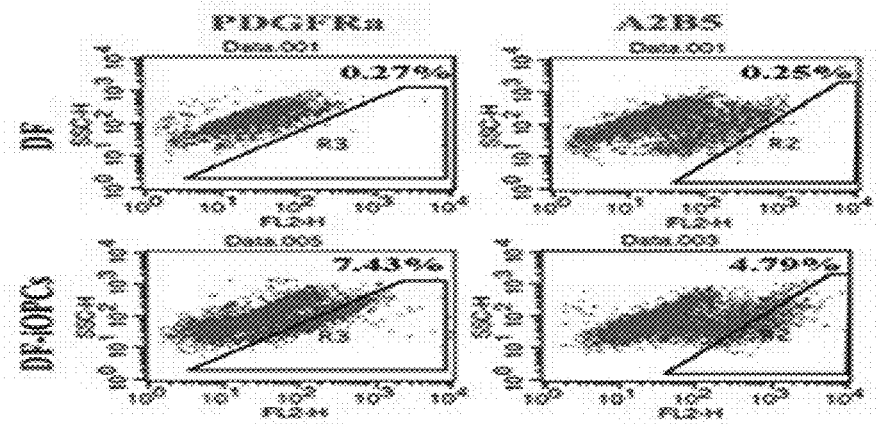
Figure 19:
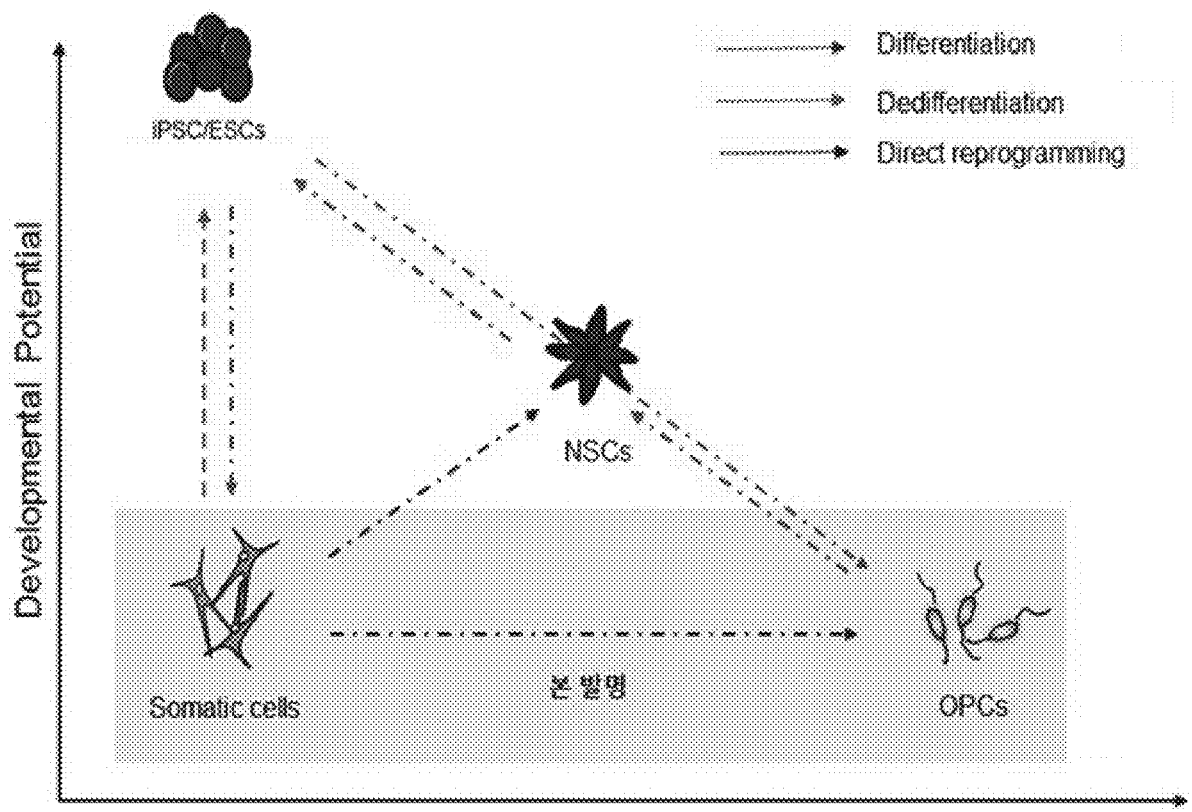
FIG. 19 is a diagram showing complete details of the present invention and the differences from the conventional art.

As a result, like the foreskin fibroblasts, the expression of PDGFRα, A2B5 and Olig2, which were representative markers for the OPCs, was confirmed by RT-PCR, immunohistochemical staining and FACS analysis (FIGS. 17 and 18).

Therefore, it was proved that the combination of Oct4 and the low molecular weight substances is an induction method which can be applied to various human somatic cells and not an induction method limited to BJ cells.

INDUSTRIAL APPLICABILITY

A method of inducing OPCs by treating Oct4-overexpressing human somatic cells with low molecular weight substances according to the present invention can establish OPCs with high efficiency in a short period of time through direct reprogramming without via neural stem cells, and thus is useful as a cell therapeutic agent of an intractable demyelinating disease. In the above, specific parts of the present invention have been described in detail.

However, it will be apparent to those of ordinary skill in the art that such detailed descriptions are just exemplary embodiments, and thus the scope of the present invention is not limited thereto. Therefore, the actual scope of the present invention will be defined by the accompanying claims and equivalents thereof.

What is claimed is:

1. A method of inducing oligodendrocyte from human somatic cells, comprising:
   (a) inducing oligodendrocyte precursor cells (OPCs) by culturing human somatic cells, into which a nucleic acid molecule encoding an Oct4 protein is introduced, in a medium containing (i) a TGF-β type I receptor inhibitor; (ii) an inhibitor of Rho-associated kinase (ROCK inhibitor); (iii) a histone deacetylase inhibitor; and (iv) a sonic hedgehog agonist (Shh agonist), and
   (b) culturing the induced OPCs in a medium containing an inhibitor of Rho-associated kinase (ROCK inhibitor), a calcium channel agonist and a leukemia inhibitory factor (LIF).

2. The method of claim 1, wherein the medium of the step further comprises a calcium channel agonist.

3. A method of inducing oligodendrocyte from human somatic cells, comprising:
(a) inducing oligodendrocyte precursor cells (OPCs) by culturing human somatic cells in a medium containing (i) a TGF-β type I receptor inhibitor; (ii) an inhibitor of Rho-associated kinase (ROCK inhibitor); (iii) a histone deacetylase inhibitor; and (iv) a sonic hedgehog agonist (Shh agonist), wherein the human somatic cells are treated with an Oct4 protein before, during or after the culture, and
(b) culturing the induced OPCs in a medium containing an inhibitor of Rho-associated kinase (ROCK inhibitor), a calcium channel agonist and a leukemia inhibitory factor (LIF).

4. The method of claim 3, wherein the medium of the step (a) further comprises a calcium channel agonist.

5. The method of claim 1, wherein the medium of the step (a) further comprises any one selected from the group consisting of RG108, BIX01294, SP600125, lysophosphatidic acid, Bayk8644, forskolin, dexamethasone, EX527 and rolipram.

6. The method of claim 1, wherein the TGF-β type I receptor inhibitor is A83-01, the ROCK inhibitor is thiazovivin, the histone deacetylase inhibitor is valproic acid, and the Shh agonist is purmorphamine.

7. The method of claim 2, wherein the calcium channel agonist is forskolin.

8. The method of claim 1, wherein the medium of the step (a) is DMEM containing N2, B27, penicillin/streptomycin, non-essential amino acids, bFGF, PDGF and ascorbic acid.

9. The method of claim 1, wherein the human somatic cells are selected from the group consisting of foreskin fibroblasts, hair-follicle dermal papillae, IMR90 lung fibroblasts and dermal fibroblasts.

10. The method of claim 1, wherein the OPCs express any one or more markers selected from the group consisting of PDGFRα, A2B5, Olig2, Sox10, S100b and ZFP536.

11. The method of claim 1, wherein the OPCs do not express Sox1, Sox2 and Pax6 markers.

12. The method of claim 1, wherein the medium of the step (b) is DMEM containing N2, B27, penicillin/streptomycin, non-essential amino acids, ascorbic acid and triiodo-1-thyronine (T3).

* * * * *